US009910958B2

United States Patent
Mielekamp et al.

(10) Patent No.: US 9,910,958 B2
(45) Date of Patent: Mar. 6, 2018

(54) METHOD AND DEVICE FOR DISPLAYING A FIRST IMAGE AND A SECOND IMAGE OF AN OBJECT

(71) Applicant: KONINKLIJKE PHILIPS N.V., Eindhoven (NL)

(72) Inventors: Pieter Maria Mielekamp, Veldhoven (NL); Nicolaas Jan Noordhoek, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 92 days.

(21) Appl. No.: 14/891,464

(22) PCT Filed: Jun. 4, 2014

(86) PCT No.: PCT/EP2014/061549
§ 371 (c)(1),
(2) Date: Nov. 16, 2015

(87) PCT Pub. No.: WO2014/195344
PCT Pub. Date: Dec. 11, 2014

(65) Prior Publication Data
US 2016/0171157 A1 Jun. 16, 2016

(30) Foreign Application Priority Data
Jun. 5, 2013 (EP) .................................. 13170650

(51) Int. Cl.
*G06F 19/00* (2011.01)
*G06T 11/60* (2006.01)
*G06T 11/00* (2006.01)
*G09G 5/02* (2006.01)
*A61B 5/00* (2006.01)
*A61B 6/00* (2006.01)

(52) U.S. Cl.
CPC ............ *G06F 19/321* (2013.01); *A61B 5/742* (2013.01); *A61B 6/463* (2013.01); *G06F 19/3406* (2013.01); *G06T 11/001* (2013.01); *G06T 11/60* (2013.01); *A61B 6/467* (2013.01); *A61B 6/5235* (2013.01); *G06T 2210/41* (2013.01)

(58) Field of Classification Search
CPC combination set(s) only.
See application file for complete search history.

(56) References Cited

U.S. PATENT DOCUMENTS

| 7,623,697 | B1 | 11/2009 | Hughes et al. |
| 8,208,483 | B2 | 6/2012 | Thyni |
| 2009/0238329 | A1 | 9/2009 | Haras |
| 2010/0245386 | A1 | 9/2010 | Gachignard |

(Continued)

OTHER PUBLICATIONS

Rehm, K. et al., "Display of Merged Multimodality Brain Images Using Interleaved Pixels with Independent Color Scales", J. Nucl Med 1994; 35:1815:1821.

(Continued)

*Primary Examiner* — Wesner Sajous

(57) ABSTRACT

The positions of the images and a display mode of at least two images of an object are selected based on a comparison of a provided distance value between the edges of the two displayed images and a distance threshold value. By continuously varying the distance value, the corresponding images and the display mode are adapted to an actual distance value.

19 Claims, 10 Drawing Sheets

(56) References Cited

U.S. PATENT DOCUMENTS

| | | |
|---|---|---|
| 2011/0157154 A1 | 6/2011 | Bernard et al. |
| 2011/0169862 A1 | 7/2011 | Darbhe et al. |
| 2012/0019548 A1 | 1/2012 | Zhu et al. |
| 2012/0059239 A1 | 3/2012 | Yamaguichi |
| 2012/0069968 A1 | 3/2012 | Core et al. |
| 2012/0155738 A1 | 6/2012 | Noordhoek et al. |
| 2012/0249533 A1 | 10/2012 | Kanagawa et al. |
| 2013/0022172 A1 | 1/2013 | Lee et al. |
| 2013/0215148 A1* | 8/2013 | Antonyuk ............ G06T 19/006 345/633 |
| 2013/0257870 A1* | 10/2013 | Kokojima ............ G06T 15/50 345/426 |
| 2015/0245819 A1* | 9/2015 | Yoshiara ................ A61B 8/06 600/424 |

OTHER PUBLICATIONS

Rosset, A. et al., "Navigating the Fifth Dimension: Innovative Interface for Multidimensional Multimodality Image Navigation", RG, vol. 26, No. 1, Jan.-Feb. 2006, pp. 299-308.

* cited by examiner

METHOD AND DEVICE FOR DISPLAYING A FIRST IMAGE AND A SECOND IMAGE OF AN OBJECT

CROSS-REFERENCE TO PRIOR APPLICATIONS

This application is the U.S. National Phase application under 35 U.S.C. § 371 of International Application No. PCT/IB2014/061549, filed on Jun. 4, 2014, which claims the benefit of European Patent Application No. 13170650.9, filed on Jun. 5, 2013. These applications are hereby incorporated by reference herein.

FIELD OF THE INVENTION

The present invention relates to a method for displaying at least a first image and a second image of an object on a display, to a computer program for carrying out a method, and to a computer-readable medium on which a computer program is stored. Furthermore, the present invention relates to a device for calculating a display mode for displaying at least a first image and a second image of an object.

BACKGROUND OF THE INVENTION

In the medical domain of presenting medical images of multi-modality volume acquisitions, the medical images may be presented and analyzed as slabs.

The document U.S. Pat. No. 8,208,483 B2 relates to a medical imaging system comprising one or more displays. Furthermore, a viewer device is described in said document, which viewer device generates an interactive user interface screen on the display and enables a user to simultaneously inspect selected image data of multiple patients or multiple images.

US 2012/0069968 A1 discloses a method and apparatus for positioning a patient for radiation treatment. The method includes obtaining a plurality of projection images of a patient positioned on a treatment couch, displaying at least one of the plurality of projection images with a corresponding synthetic projection image on a display, adjusting the position of the at least one projection image on the display to approximately align with the corresponding synthetic projection image in response to a user dragging the at least one projection image on the display with a user interface device, and moving the treatment couch to position the patient based on position adjustments of the at least one projection image.

US 2009/0238329 A1 discloses a method and device for medical imaging, a number of input parameters with regard to an image exposure are imported into a controller of the imaging device, that associate a desired image quality with a defined image exposure region. A number of control parameters are determined corresponding to each input parameter. The controller supplies each control parameter to the image acquisition apparatus for acquiring the image exposure of the examination region with desired local image quality.

SUMMARY OF THE INVENTION

It may be seen as an object of the present invention to enable an improved analysis and/or an improved displaying of medical images.

The described embodiments similarly pertain to the method, the computer program, the computer-readable medium, and the device, although specific embodiments may be explained in detail in the following with respect to a method or a device only. Synergetic effects may arise from different combinations of the embodiments although they might not be described in detail hereinafter.

According to an exemplary embodiment of the invention, a method for displaying at least a first image and a second image of an object on a display is presented. Said method comprises the steps of providing a distance value between an edge of the first image and an edge of the second image of the object. Moreover, the method comprises the step of displaying a side by side view of the first image and the second image on the display in case the provided distance value exceeds a distance threshold value, wherein a distance between the edge of the displayed first image and the edge of the displayed second image corresponds to the provided distance value; or displaying an overlay view of the first image and the second image in case the provided distance value is less than the distance threshold value.

If desired, the method may comprise the steps of providing the first image representing a first volume of the object and providing the second image representing a second volume of the object.

Hereinafter, the first image and the second image may refer to two distinct images. Furthermore, the first image and the second image may also refer to a combination of the first image and the second image. Thus, the overlay view should also be understood as a displaying of the first image and the second image.

Thus, it may be seen as an aspect of the invention to provide for a method for controlling the image display of medical images. A further aspect of the invention is to provide for a method, which is supported by a computer implemented user interface, to react to a user input defining a distance value between displayed images and to display a combination of two images based on said distance value. In other words, the method provides for an automated adaption of two different displaying modes of two images, which images may represent one or more volumes of the object. For example, such an automated adaption can be performed by calculating which display mode shall be used on the basis of a predetermined threshold value and an actually determined or an actually provided distance value. Therein the two modes of displaying are a side by side view and an overlay view.

The object, images of which are used by the present invention, may refer to any object from which medical images can be displayed. For example, the object may refer to a human body, an animal body, or a medical sample.

The first image may be an image representing a first volume of the object and the second image may be an image representing a second volume of the object. Hereinafter, the first volume and the second volume of the object may refer to the same volume of the object. For example, the first volume and the second volume refer to the same volume at different points in time. Moreover, the first volume and the second volume may refer to different volumes.

The volume of the object may refer to a partial volume of the object. For example, the volume is a slab. A slab may refer to a thick slice of the object and may be defined in terms of a position and an orientation of a plane and a thickness. In order to display the slab, the slab may be rendered on a display and may be resampled using a model-view-projection transformation and a selected rendering function. The slab on the display may be presented orthogonal to the viewing direction. This will become apparent from and elucidated with the following detailed explanations. For example, a slab is a combination of multiple slices. The method step of providing a distance value may refer to the step of receiving a distance value. For example, the distance value may be provided by a distance value input device. In particular, the distance value input device may be embodied as a keyboard, a mouse, a graphical representation of a button, or as a microphone. In case the distance value input device is a microphone, the distance value may be provided acoustically such that the distance value may be provided without having to handle an input device.

FIG. 1 shows an object used in accordance with an exemplary embodiment of the present invention, which object comprises a first volume and a second volume. In FIG. 2, a flow diagram for a method for displaying at least a first image and a second image of an object is shown. FIG. 3 shows an exemplary embodiment assembly comprising a device for carrying out the herein presented method.

The first and second image may refer to first and second image data. For example, the data can be stored in and provided by a database. The present invention may make use of a communication between the device of the present invention and the data base to submit desired and or necessary data, like e.g. image data. Thus, the step of providing the first image and the second image may refer to the step of providing first image data and second image data. The first and second image data may thus be sent to a displaying device, for example, a screen. The first and second image may each comprise a plurality of voxels, i.e. a plurality of 3 dimensional picture elements. However, also other image data formats may be used. For example, 2 dimensional data may be used in addition or alternatively.

The steps of displaying the first image and the second image may thus refer to or may be seen as sending first image data and second image data to a displaying device and/or to calculating a screen image comprising the first image and the second image based on first image data and second image data. The side by side view may refer to a displayed image where the first image is located next to the second image. In other words, the first image and the second image are presented in different regions of the display. They may be displayed adjacent from each other with an adjustable separation range. However, in the overlay view, the first image may be presented over the second image or vice versa. Furthermore, the first image and the second image may be combined such that both features of the first image and of the second image are visible in the overlay view. In other words, the overlay view may comprise a superposition of the first image and the second image.

The first volume and the second volume may be registrated in a same frame of reference, e.g. a patient coordinate space in, for example, millimeters. During the displaying of the volumes comparable slices of the volumes can be resampled based on a definition of the volumes and the orientation of the resampling planes. For example, the sampling planes through the volumes are aligned orthogonal to the caudal-cranial direction, i.e. the feet to head direction. The step of providing the distance value between an edge of the first image representing the first volume and an edge of the second image representing the second volume of the object can be carried out, for example, by a distance value input device. Such a distance value input device may be initialized at a starting position, which may represent a distance value which is larger than the distance threshold value. However, also other initializations can be used without departing from the present invention.

The method according to the present invention may facilitate to interactively browse, zoom and rotate through the images. The sizes of the rendered images may change depending on the orientation, the zoom-factor and the position of the volumes. By changing the distance value between the images, the presentations may be lined-up more closely. While browsing through the images, a side by side view may offer maximum contrast and/or brightness resolution and/or an optimal coherent global impression of the individual images. Furthermore, an overlay view may offer a clearer distinctive view on local image differences.

The distance threshold value may define a threshold value which defines a transition between the side by side view and the overlay view.

According an exemplary embodiment of the present invention, the provided distance value is compared with the distance threshold value and a side by side view or an overlay view is displayed based on said comparison. For example, the distance threshold value can be equal to zero. If the distance threshold value is zero, the overlay mode is activated when the first image and the second image fully overlap. However, also other values different from zero can be used. Thus, the overlay view may be activated when the first image and the second image partially overlap. The distance threshold value may be stored in the database or may also be received as an input from the user and can be processed accordingly.

The displaying of the first image and the second image based on a comparison of the provided distance value and the distance threshold value may alternatively be provided by the steps of displaying a side by side view of the first image and the second image on the display in case the provided distance value is larger than a distance threshold value; and displaying an overlay view of the first image and the second image in case the provided distance value is less than the distance threshold value. The user may also select which display mode he prefers in case the provided distance value is equal to the threshold value of the distance. Both options, the side by side view and the overly view can be used in case the provided distance value is equal to the threshold value of the distance.

The present invention may thus overcome problems which arise when using the side by side view or the overlay view of multiple images separately. On the one hand, a drawback of only using the side by side view may be that detailed voxel-level comparison could be difficult. On the other hand, the overlay view may be sensible to image mismatches, motion artifacts, and to image lost due to a lack of contrast. Thus by combining the side by side view and the overlay view of multiple images on the basis of the provision of a distance value, the problems of the side by side view may be overcome by the overlay view and vice versa.

Therefore, the previously described method may be seen as a method in which a distance value is determined and in which a first image and a second image of a respective first and second volume of the object are provided. Furthermore, the displaying of a side by side view of the first image and the second image is comprised in case the distance value is larger than a threshold value. Alternatively, an overlay view of the first image and the second image is displayed by the presented method in case the distance value is less than a threshold value. If desired, the first image and the second image may be selected such that the distance between the displayed first image and the displayed second image is closest to the determined distance value.

According to yet another exemplary embodiment of the invention, the first image is obtained with the method selected from the group comprising three-dimensional or rotational angiography, XperCT, X-ray computed tomography, magnetic resonance tomography, positron emission tomography, and any combination thereof; and the second image is obtained with the method selected from the group comprising three-dimensional rotational angiography, XperCT, X-ray computed tomography, magnetic resonance tomography, positron emission tomography, and any combination thereof.

In other words, the method provides a displaying of comparable multi-modality images, which may be retrieved from a database based on a patient's identification data. The respective generation of such images may be part of a further exemplary embodiment of the presented method.

According to a further embodiment of the present invention, the first image is obtained with a different imaging method than the second image.

According to another exemplary embodiment of the present invention, the method further comprises the steps of rendering the first image using maximum intensity projection or multiplanar rendering and rendering the second image using maximum/minimum intensity projection or multiplanar average rendering.

According to a further exemplary embodiment of the present invention, the method further comprises the steps of rendering the first image with a first transfer function; and rendering the second image with a second transfer function. The first transfer function may be coupled to the second transfer function in case the provided distance value is less than the distance threshold value.

The transfer function, also known as window-width/level function, e.g., maps voxel densities to color/grey values. It may provide an interactive way to zoom-in on a limited range of voxel densities. In this way, an optimal view by concentrating on typical voxel densities, like bony versus soft tissue information may be provided. Furthermore, the transfer function may offer a way to focus on certain image feature like tumors in organs or to follow the up-take of small amounts of embolization materials like radiopaque contrasts agents or imageable beads during embolotherapy.

According to a further exemplary embodiment of the present invention, the method further comprises the steps of continuously amending the distance value by means of a distance value determining device and continuously adapting the displaying of the first image and the second image simultaneously to the continuous amendment based on the distance value, respectively.

The step of continuously amending the distance value by means of a distance value determining device may be performed by means of a sliding tool, which sliding tool is, for example, shown on the display device. Said sliding tool may be operated by means of a pointing device, for example, a mouse. Of course, other embodiments of the distance value determining device are possible.

Thus, an aspect of the present invention is to provide an automatic method of providing a displayed image based on a continuous amendment of the distance value. The method comprises at least two different display modes, which are displayed based on the relation between the provided or determined distance value and the distance threshold value. When the distance value is amended by means of the distance value determining device, the displaying of the first image and the second image may be adapted such that the displayed first image and the displayed second image have a distance that essentially corresponds to the amended and/or actual distance value set by or by means of the distance value determining device.

According to another exemplary embodiment of the invention, the first image and the second image are represented in different regions of the display in the side by side view. Furthermore, in the overlay view, the first image and the second image are combined and represented in the same region of the display. This will become more apparent from the description of the figures.

According to a further exemplary embodiment of the invention, the method further comprises the step of adding a first color information and/or a first brightness information of the first image to a second color information and/or a second brightness information of the second image in case the provided distance value is less or equal to the distance threshold value.

The first image may comprise at least a first value representing a color information and/or a first intensity value representing a first intensity information. For example, each pixel of the first image comprises an RGB triplet (R, G, B) comprising color information of the respective pixel and an alpha value, which comprises the opacity information. Equally, each pixel of the second image may comprise an RGB triplet as well as an alpha value. The combination of the first image and the second image in the overlay view may be achieved by adding the RGB triplets of each overlaying pixel of the first image and the second image.

In the overlay view, the images may be displayed on top of each other making use of the additive characteristics of the RGB pixel values. In this way, overlapping contrasted image features will contain both colors while distinct features will maintain their original colors. The combination of the images may be independent of their overlapping order.

According to another exemplary embodiment of the invention, the method further comprises the steps of providing a volume of interest of the object by means of volume metadata, selecting a first volume from the volume of interest, and selecting a second volume from the volume of interest.

In other words, a volume of interest of the object, which is to be analyzed, may be selected. Said volume of interest may comprise the first volume as well as the second volume. The first volume and the second volume may refer to the same volume. Moreover, the first volume and the second volume may refer to the same volume at different points in time. For example, the first volume and the second volume are parallel slabs of the volume of interest.

According to a further exemplary embodiment of the invention, a superposition of the first image and the second image is displayed in the overlay view. Furthermore, in the overlay view, the first image is rendered with a first color and the second image is rendered with a second color and the first color is different than the second color.

In other words, the first image is colored with a first color and the second image is colored with a second, different color. Thus, in the overlay view, features of the first image are visible in the first color and features of the second image are visible in the second color. Furthermore, features that are the same in the first image and the second image are shown in a third color, wherein the third color is a mixture of the first color and the second color. Thus, it is possible to assign the features to the first image and/or to the second image. Furthermore, it is also possible to identify the differentiating features between the first image and the second image as well as to identify equal features of the first image and the second image.

According to another exemplary embodiment of the invention, the first color is complementary to the second color.

In other words, the first color and the second color are defined such that a mixture of the first color and the second color will result in white. Thus, in the overlay view, features of the first image that are equal to features of the second image may be displayed in white. For example, the first color is red, the second color is cyan, and the combination of the first color and the second color is white.

According to another embodiment of the invention, the method further comprises the steps of providing a second distance value between an edge of the second image and an edge of a third image of the object. The method further defines a step of displaying a side by side view of the second image and the third image on the display in case the provided second distance value exceeds a second distance threshold value, wherein a distance between the edge of the displayed second image and the edge of the displayed third image corresponds to the provided second distance value. Furthermore, the method comprises the steps of displaying an overlay view of the second image and the third image in case the provided second distance value is less than the second distance threshold value; or displaying an overlay view of the first image, the second image, and the third image in case the provided first distance value is less than the first distance threshold value and the provided second distance value is less or equal to the second distance threshold value. Moreover, the method may comprise the step of providing a third image representing a third volume of the object.

The user may also select which display mode he prefers in case the provided distance value is equal to the threshold value of the distance. Both options, the side by side view and the overlay view can be used in case any of the provided distance values is equal to the respective threshold value.

Thus, the method provides a first image representing a first volume, a second image representing a second volume, and a third image representing a third volume of the object. Therein the first distance between an edge of the first image and an edge of the second image as well as the second distance between an edge of the second image and an edge of the third image of the object is configurable and/or adjustable for the user. Corresponding adjustment means, like a first and a second distance value determining device can be provided by the present invention. In other words, first the first distance value and the second distance value are provided and then the first image, the second image, and the third image are displayed based on the first distance value and the second distance value. As has been described before, a corresponding comparison between the received or determined distance value and the associated/corresponding distance threshold value can be carried out, i.e. calculated, according to the present invention.

Thus, an extension and generalization of the method for or to three images of an object is presented.

By using a plurality of volumes typical image attributes, which are optimally presented by one imaging modality such as MR or PET, may be combined with image attributes like high resolution anatomical details represented or available by images of another modality such as pre-interventional (Xper)-CT, in combination with interventional XperCT image data showing interventional materials, like ablation needles, imageable beats, stents etc.

Apparently, the herein presented systematic of the method of the present invention can also be applied in an analogue way to four, five and even more images of the desired object.

According to an exemplary embodiment of the invention, a computer program element for displaying at least a first image and a second image of an object on a display is presented, which computer program element, when being executed by a processor, is adapted to carry out any of the above-defined methods.

The computer program element may be part of a computer program, but it can also be an entire program by itself. For example the computer program element may be used to update an already existing computer program to get to the present invention.

According to another exemplary embodiment of the invention, a computer-readable medium on which a computer program element is stored, wherein the computer program element enables a processor to carry out any of the above-defined methods, is presented.

The computer readable medium may be seen as a storage medium, such as for example, a USB stick, a CD, a DVD, a data storage device, a hard disk, or any other medium on which a program element as described above can be stored.

According to another exemplary embodiment of the invention, a device for calculating a display mode for displaying at least a first image and a second image of an object is presented, wherein the device comprises a processor. Furthermore, the device is configured to receive data of a distance value between an edge of the first image and an edge of the second image of the object. In case the distance value exceeds a distance threshold value, the processor is configured to generate a first display signal comprising information of a side by side view of the first image and the second image, wherein a distance between the edge of the displayed first image and the edge of the displayed second image corresponds to the provided distance value. In case the distance value is less than the distance threshold value, the processor is configured such that a second display signal is generated comprising information of an overlay view of the first image and the second image.

For example, in FIG. 3, an exemplary assembly comprising a device for calculating a display mode for displaying at least a first image and a second image of an object is shown.

In general, the data of the distance value between an edge of the first image and an edge of the second image may be a number defining said distance between the edge of the displayed first image and the edge of the displayed second image. Furthermore, the data of the distance value may also refer to a coordinate or a set of coordinates in order to control a distance value input device, for example, a sliding element on a display, which can be controlled by means of, e.g., a mouse.

The selection step of a first or second image performed by the processor may refer to a database query such that the first image and the second image can be retrieved from the database.

A first display signal may enable and/or cause a display device to show an image on a screen with a side by side view of the first image and the second image. In other words, the first image and the second image are located in different regions of the screen image. Equally, the second display signal enables and/or causes the display to show a screen image with an overlay view of the first image and the second image. Thus, in the overlay view, the screen image may comprise a superposition of the first image and the second image. Therefore, a control loop of the display is presented based on the input regarding the distance between the edge of the first image and the edge of the second image and based on the distance threshold value.

According to another exemplary embodiment of the invention, the device further comprises a display device configured to display the first display signal and the second display signal; and a distance value determining device configured determine the distance value and to create the corresponding data of the distance value.

The display device may refer to a computer display, a display of a mobile device, or to an image which is projected by a beamer. Moreover, the display device may refer to a touch screen such that, e.g., the display device and the distance value determining device are incorporated by the same device. The distance value determining device may refer to the usual input devices such as a keyboard or a mouse. Furthermore, the distance value determining device may also refer to a microphone such that the distance value may be provided during an operation or examination.

The present application describes an automatic method for displaying images of an object. By providing a distance value between a displayed first image and a displayed second image, a displaying mode of the first image and the second image is determined. Thus, by controlling and/or selecting the distance value and/or the distance threshold value, the display mode is automatically selected. This may improve the image analysis for the medical practitioner.

It has to be noted that the embodiments of the invention are described with reference to the different subject-matters. In particular, some embodiments are described with reference to device type claims whereas other embodiments are described with reference to method type claims. However, a person skilled in the art will gather from the above and the following description that unless other notified in addition to any combination of features belonging to one type of subject-matter, also any combination between features relating to different subject-matter is considered to be disclosed with this application.

The aspects described above and further aspects, features and advantages of the invention may also be found in the example embodiments which are described in the following with reference to the appended drawings.

BRIEF DESCRIPTION OF THE DRAWINGS

Exemplary embodiments of the invention will be described in the following drawings. Any reference signs in the claims should not be construed as limiting the scope of the claims.

DETAILED DESCRIPTION OF THE EMBODIMENTS

Figure 1:
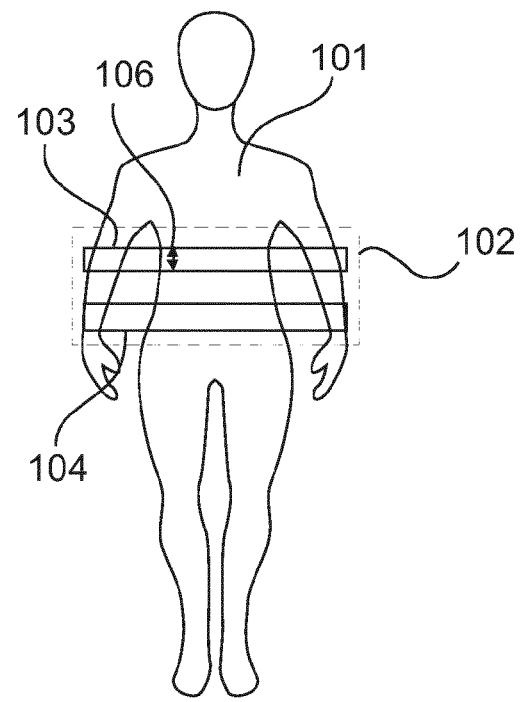
FIG. 1 is a schematic drawing of a human body which can be used for understanding the present invention.
Figure 2:
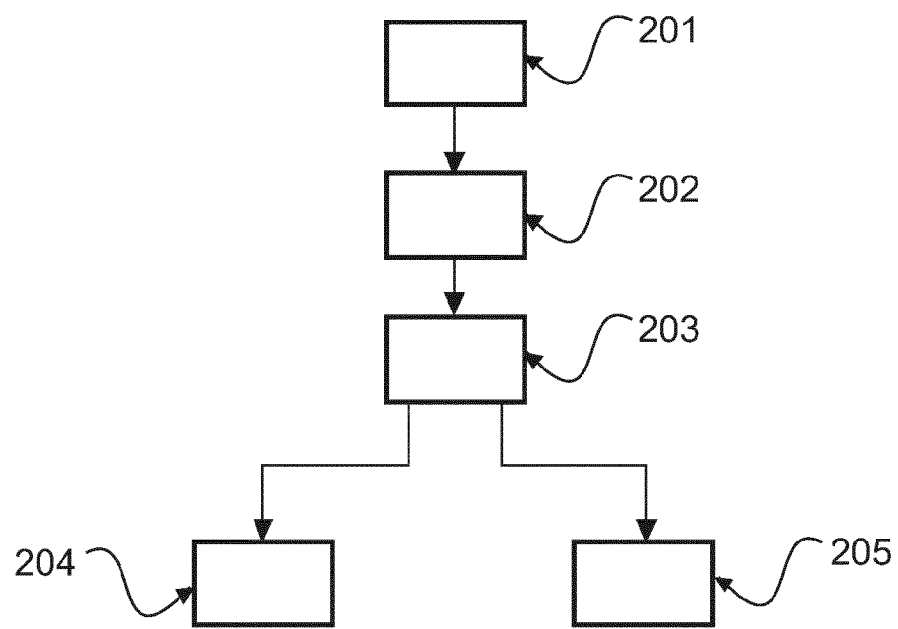
FIG. 2 shows a flow-chart according to an exemplary embodiment of the present invention.

FIG. 1 shows a contour of a human body 101 comprising a volume of interest 102 that can be used in accordance with an exemplary embodiment of the present invention. The volume of interest 102 comprises a first volume 103 and a second volume 104. A first image and second image may be taken from the first volume 103. Alternatively, the first image may be rendered on the basis of the first volume 103 and the second image may be rendered on the basis of the second volume 104. The first volume 103 has a thickness 106. The region of interest or volume of interest 102 may represent a part of the body 101 which is scanned by means of an imaging method. Exemplarily, the imaging method may be selected from the group comprising three-dimensional rotational angiography, XperCT, X-ray computed tomographic, magnetic resonance tomography, positron emission tomography, and any combination thereof. FIG. 2 shows a flow-chart for a method for displaying at least a first image and a second image of an object on a display. The method comprises the steps of providing a distance value between an edge of the first image and an edge of the second image of the object which step is shown with reference sign 201. Moreover, providing a first image representing a first volume of the object is depicted with 202 and providing a second image representing a second volume of the object with 203. Displaying a side by side view of the first image and the second image on the display in case the provided distance value exceeds a distance threshold value, wherein a distance between the edge of the displayed first image and the edge of the displayed second image corresponds to the provided distance value, is shown with step 204. Alternatively, displaying an overlay view of the first image and the second image in case the provided distance value is less than the distance threshold value is carried out in step 205. The first volume and the second volume may describe the same or different volumes of the object. Moreover, the first volume and the second volume may relate to the same volume of the object scanned at different points in time.

Steps 202 and 203 shall not be construed as being essential. In other words, also a method comprising only the steps 201, 204, and 205 is herewith disclosed, as has been described before in the context of an exemplary embodiment and is described in the claims. The method steps 201, 202 and 203 may be performed in the order shown in FIG. 2. The method steps 202 and 203 may also be performed at the same time, i.e. in parallel to each other. Furthermore, the method steps may also be performed in a different order. The method of FIG. 2 may be seen as a method for controlling the image display of medical images based on the actually given and desired distance value.

Figure 3:
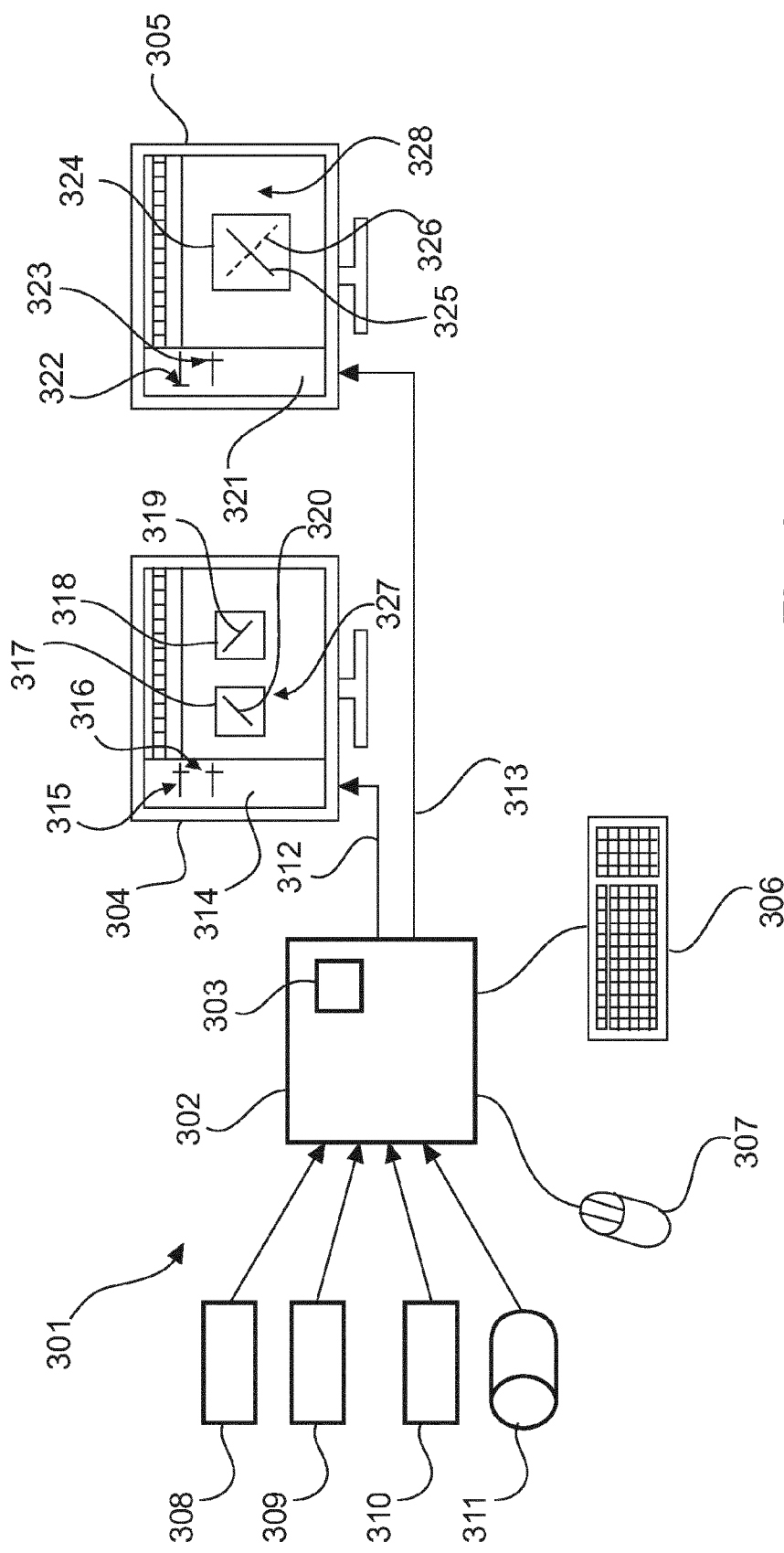
FIG. 3 shows a schematic drawing of a device according to an exemplary embodiment of the present invention.

FIG. 3 shows a schematic drawing of an assembly for calculating and for displaying a display mode of at least a first image and a second image of an object according to an exemplary embodiment of the invention. The assembly 301 comprises a device 302 for calculating a display mode for displaying at least the first image and a second image of an object 101 and comprises a processor 303 which performs or controls the method steps. For carrying out the method which is, for example, described with reference to FIG. 2, the device 302 is configured to receive data 308 of a distance value between an edge of the first image and an edge of the second image. Furthermore, the device 302 may be configured to receive data 309 of a distance threshold value and/or data 310 defining a region of interest 102 of the object 101. Furthermore, the device 302 is configured to receive image data for the first image and the second image from a database 311. In case the distance value exceeds a distance threshold value, the processor 303 is configured to generate a first display signal 312 comprising information of a side by side view 327 of the first image and the second image. In case the distance value is less than the distance threshold value, the processor 303 is configured to generate a second display signal 313 comprising information of an overlay view 328 of the first image and the second image. The device 302 may be connected to a display 304 and/or 305. FIG. 3 may also be understood such that only one display is used and 304 and 305 depict different situations of one single display. There is also a feedback signal provided from the display or displays 304 and 305 to the device 302 regarding the distance value. However, this signal feedback is not shown in FIG. 3. Furthermore, the device 302 may be connected to input devices such as a mouse 307 and/or a keyboard 306. In the exemplary embodiments shown hereinafter, the distance threshold value is exemplarily set as being equal to zero. However, this has not to be seen to restrict the distance threshold value to zero in general. The same functionality is achievable for a distance threshold value being non equal to zero. The first display signal 312 comprises data, which, when sent to a display device 304, enables and/or cause the display device 304 to show a displayed image 327, which is a side by side view. For example a user interface with a toolbar 314 may be comprised. The toolbar 314 comprises a first sliding tool 315 for controlling the distance value and a second sliding tool 316 for controlling the thickness of the slab and/or the volumes. Said first and second sliding tools 315 and 316 may be operated with the mouse 307. In the displayed image 327 it is shown that the sliding tool 315 indicating the distance value is configured to a value larger than zero, i.e. larger than the distance threshold value. Consequently, a first image 317 and a second image 318 are shown in a side by side view. The first image 317 comprises an exemplary and symbolic first feature 320 and a second image 318 comprises an exemplary and symbolic second feature 319.

The second display signal 313 comprises data, which, when sent to a display device 305, enables and/or cause the display device 305 to show a displayed image 328, which is an overlay view. For example, a user interface with a toolbar 321 is comprised. The toolbar 321 comprises a first sliding tool 322 for controlling the distance value and a second sliding tool 323 for controlling the thickness of the slab. In the displayed image 328, the first sliding element 322 indicates that the provided distance value is equal to zero. Consequently, an overlay view of the first image and the second image is shown. Thus, it becomes clear that signal is sent from the displays 304 and 305 to the device 302 regarding the respective distance value. The overlay view comprises a superposition 324 of the first image and the second image. The superposition 324 comprises the feature of the first image 325 and the feature of the second image 326. For example, the first feature 325 is shown with a different characteristic as the second feature 326. For example, the first feature 325 is shown as a straight line and the second feature 326 is shown as dashed line. The different characteristics may also be different colors. For example, the first feature 325 may be displayed in a first color, e.g., in red and the second feature 326 may be displayed in a second color, e.g., in blue. In the exemplary embodiments shown hereinafter, exemplary features are shown as hatched regions. Different hatched regions may also refer to regions with different colors and/or brightness. Cross hatched regions may refer to regions comprising a mixture of two colors.

Figure 4:
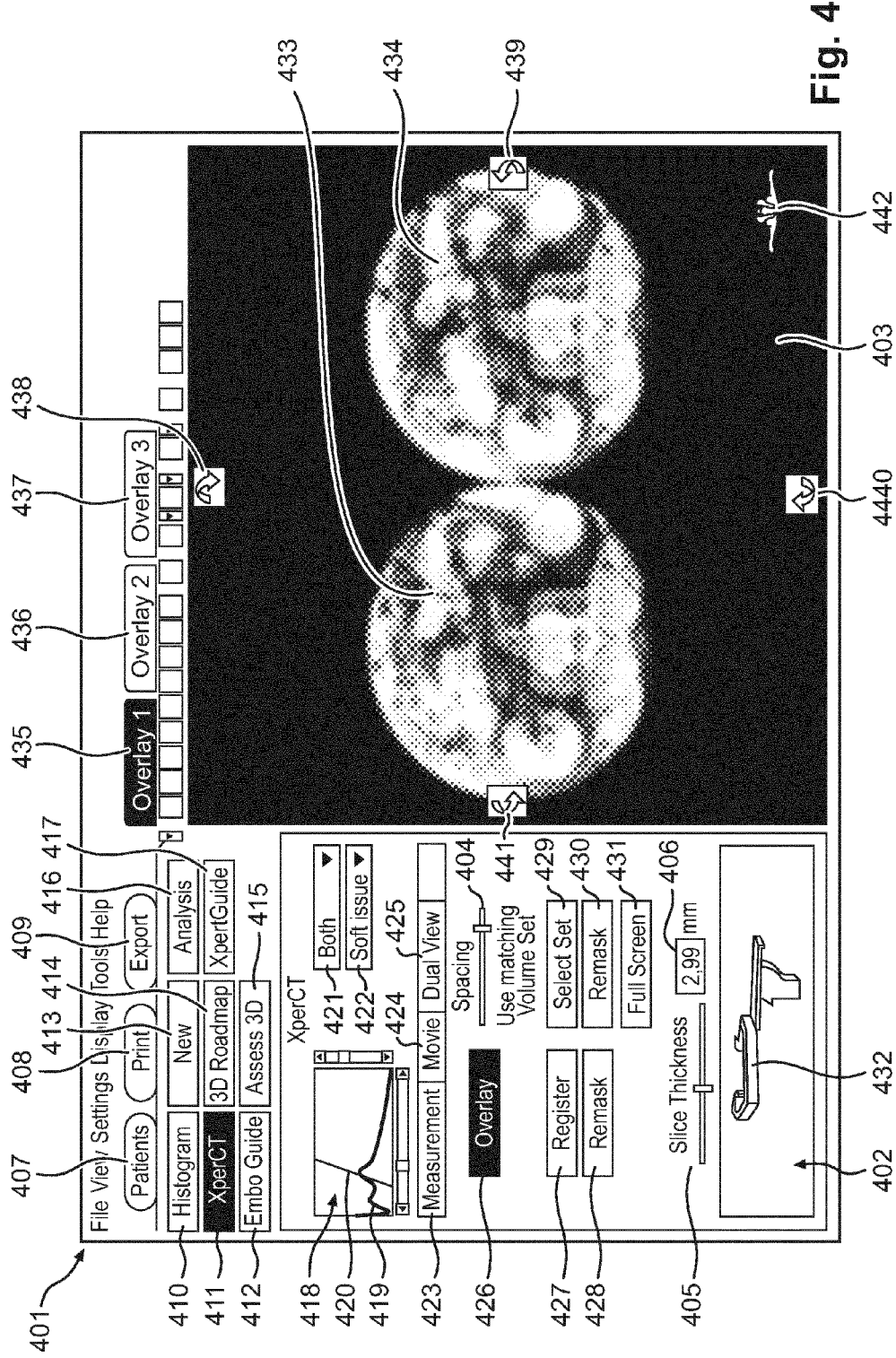
FIG. 4 shows a schematic drawing of a display view according to an exemplary embodiment of the present invention.

FIG. 4 shows a schematic display view 401 according to an exemplary embodiment of the present invention. In particular, a side by side view of the first image 433 and the second image 434 is shown. The display view 401 comprises a controlling section 402 and an image displaying section 403. The controlling section comprises a first sliding tool 404 for controlling the distance value between an edge of the first image and an edge of the second image, wherein the first image and the second image are images of a slab. A second sliding tool 405 is configured to control the thickness of the slab. Furthermore, the thickness of the slab may be configured by means of an input field 406 where the slab thickness may be entered in terms of a number. Furthermore, the controlling section 402 comprises multiple buttons, which may be provided in various different combination representing different corresponding embodiments. Thus, FIG. 4 shall not be construed such that all buttons and functions are essential for the working principle of the underlying embodiment. In the following, a short description of the different buttons as well as of the associated functions is given. The button 407 may be selected to choose the patient out of the patient database, whose images shall be displayed. The button 408 may be selected to print the images. With the button 409, the image data may be exported for being imported in other programs. Buttons 410 to 416 will offer different tools available to the practitioner. Button 410 starts the histogram function, button 411 the XperCT function, button 412 the EmboGuide function, button 413 the New function that allows zoomed reconstruction, button 414 the 3D Roadmap function, button 415 the Assess 3D function, button 416 the Analysis function and button 417 the XperGuide function. In the field 418, the transfer function 419 and the line 420 are shown. In the dropdown selection field 421 it is indicated that the same transfer function shall be used for both images. With the dropdown field 422, the transfer function can be selected. Button 423 may be selected to start the Measurement function, button 424 to start the Movie function, and button 425 to start the Dual View function. Button 426 may be selected to start the Overlay function, button 427 the Register function, button 428 the Remask function, button 429 the Select Set function, button 430 the Remask function, and button 431 the Fullscreen function. In the field 432, a schematic illustration of the orientation of the imaging device is shown. In the present exemplary embodiment, the functions XperCT and Overlay are selected.

The Overlay function may select the last used (right-side) secondary volume together with belonging registration and transfer function information. The Registration function may start the registration dialog for the manual and/or automatic 3D-3D registration. The Remask function may allow the selection of the overlay volume from a set of available secondary volumes. By means of the Select Set function matching volumes such as PET volumes, or derived/processed volumes acquired in the same frame of reference as the current selected secondary volume, can be selected re-using the registration information. The Fullscreen function may represent the image information in full-screen mode as shown in FIG. 6, getting rid of the graphic dialogs.

The image display section 403 comprises a first tab 435 for displaying a first overlay, a second tab 436 for displaying a second overlay, and a third tab 437 for displaying a third overlay. In the present exemplary embodiment the first tab 435 showing the first overlay is selected. Furthermore, a first image 433 and a second image 434 are shown. The first image 433 and the second image 434 may represent a first volume 103 of the object 101. The orientation of the volume 103 in the object 101 may be changed by means of the first rotation button 438, the second rotation button 439, the third rotation button 440, and the fourth rotation button 441. The actual orientation of the first volume 103 with respect to the object 101 is shown by means of the graphical illustration 442. In other words, the graphical illustration 442 shows the viewing direction. In the displayed image 401, a configuration is shown where the sliding tool 404 shows a distance value, which is greater than zero, i.e. greater than the threshold value.

Figure 5:
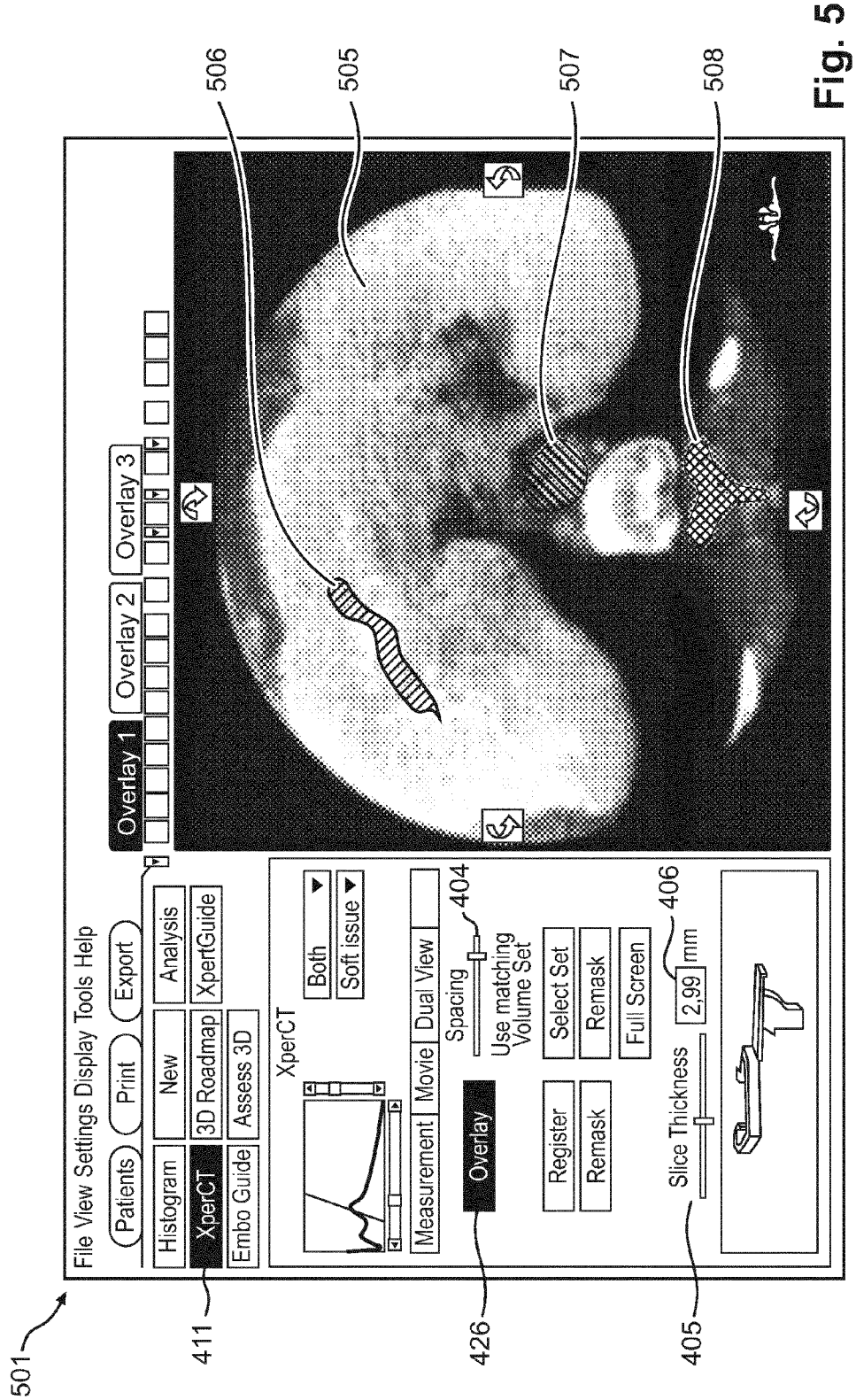
FIG. 5 shows a schematic drawing of a display view according to an exemplary embodiment of the present invention.

In FIG. 5, a displayed image 501 according to an exemplary embodiment of the invention is shown, wherein, in the overlay view, a superposition of the first image and the second image is displayed. Exemplarily the first image is rendered with a first color and the second image is rendered with a second color, and wherein the first color is different than the second color. In the controlling section, the button 411 for the function XperCT is selected. Furthermore, the button 426 for the Overlay function is selected. The second sliding element 405 for the slab thickness is configured to a slab thickness of 2.99 mm, which value is shown in the text field 406. The first sliding element 404 shows that the distance value between an edge of the first image and an edge of the second image is equal to zero, i.e. less or equal to the distance threshold value. Since the distance value between the edge of the first image and the edge of the second image of the object 101 is equal to zero and therefore less or equal to the distance threshold value, an overlay view of the first image and the second image is shown in the image displaying section. The overlay view is a superposition 505 of the first image and the second image. In the superposition 505, features 506 of the first image are shown with a first characteristic, for example, with a hatching in a first direction. Features 507 of the second image are shown with a second characteristic, for example, with a hatching in a second direction. Furthermore, features 508 which are the same in the first image and in the second image are shown with the first characteristic and with the second characteristic. For example, the feature 508 is shown with a cross hatching. The different hatching in the first direction may refer to a first color and the hatching in the second direction may refer to a second color. The cross hatching may refer to a mixture of the first color and the second color. Thus, in the overlay view, the different features can be identified and assigned to the first image and/or to the second image. Furthermore, it may be identified, which features are different in the first image and in the second image and which features are the same in the first image and in the second image.

Figure 6:
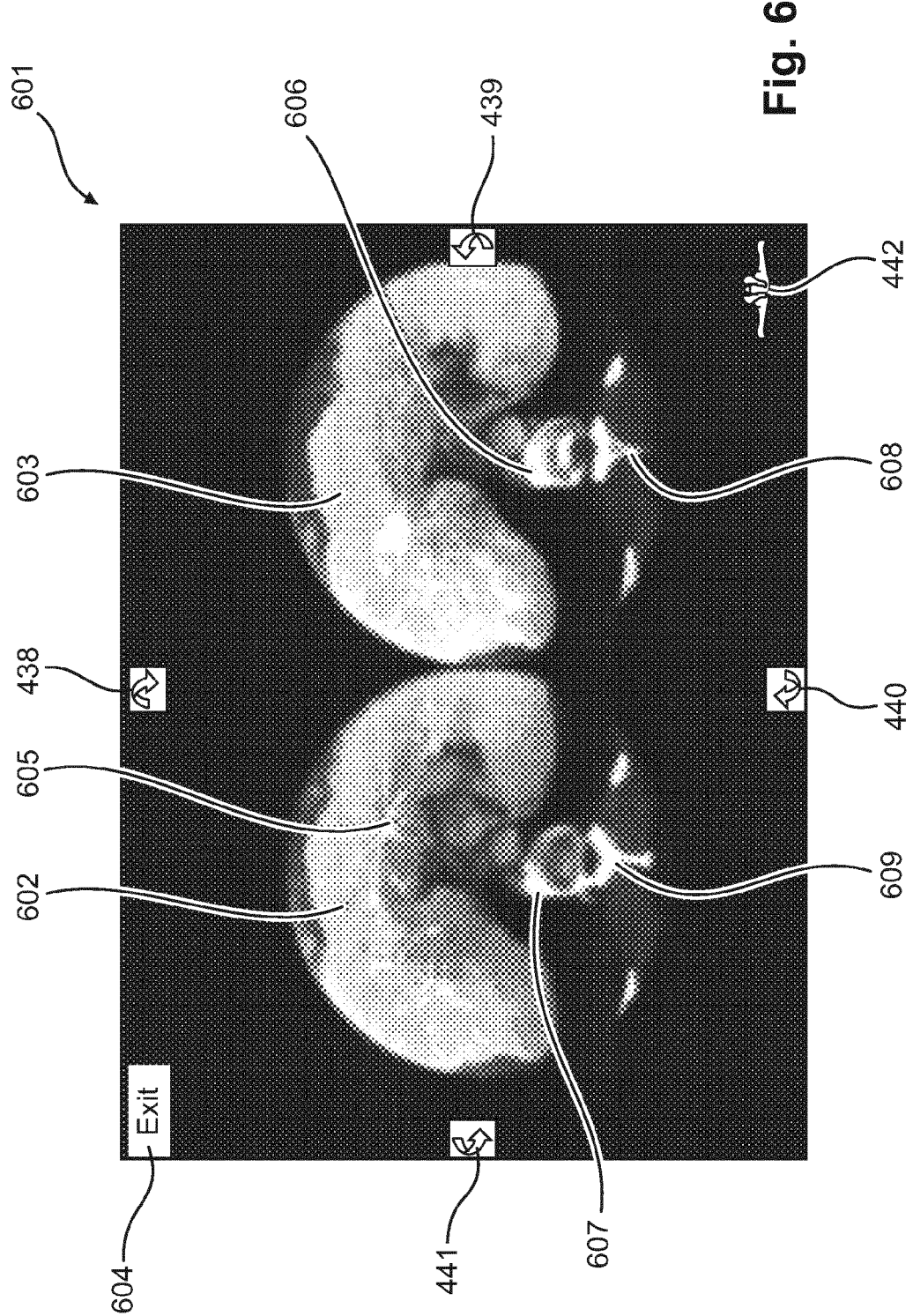
FIG. 6 shows a schematic drawing of a display view according to an exemplary embodiment of the present invention.

FIG. 6 shows a displayed image 601 of a full screen view according to an exemplary embodiment of the invention. The displayed image 601 shows a side by side view of a first image 602 and a second image 603 based on a given combination of a desired distance between an edge of the displayed first image 602 and an edge of the displayed second image 603 and a given threshold value for the distance. The first image 602 comprises features 605, 607, and 609. The second image 603 comprises the features 606 and 608. The feature 605 is only visible in the first image 602. Furthermore, it is visible that the feature 607 and the feature 606 differ from each other since there is a distance between the first volume 103 and the second volume 104. Equally, the features 609 and 608 differ from each other. With the button 604, the full screen view can be quit. With the buttons 438, 439, 440, and 441, the orientation of the first volume 103 in the object 101 can be changed. The actual orientation of the first volume 103 with respect to the object 101 is shown in the graphical illustration 442.

Figure 7:
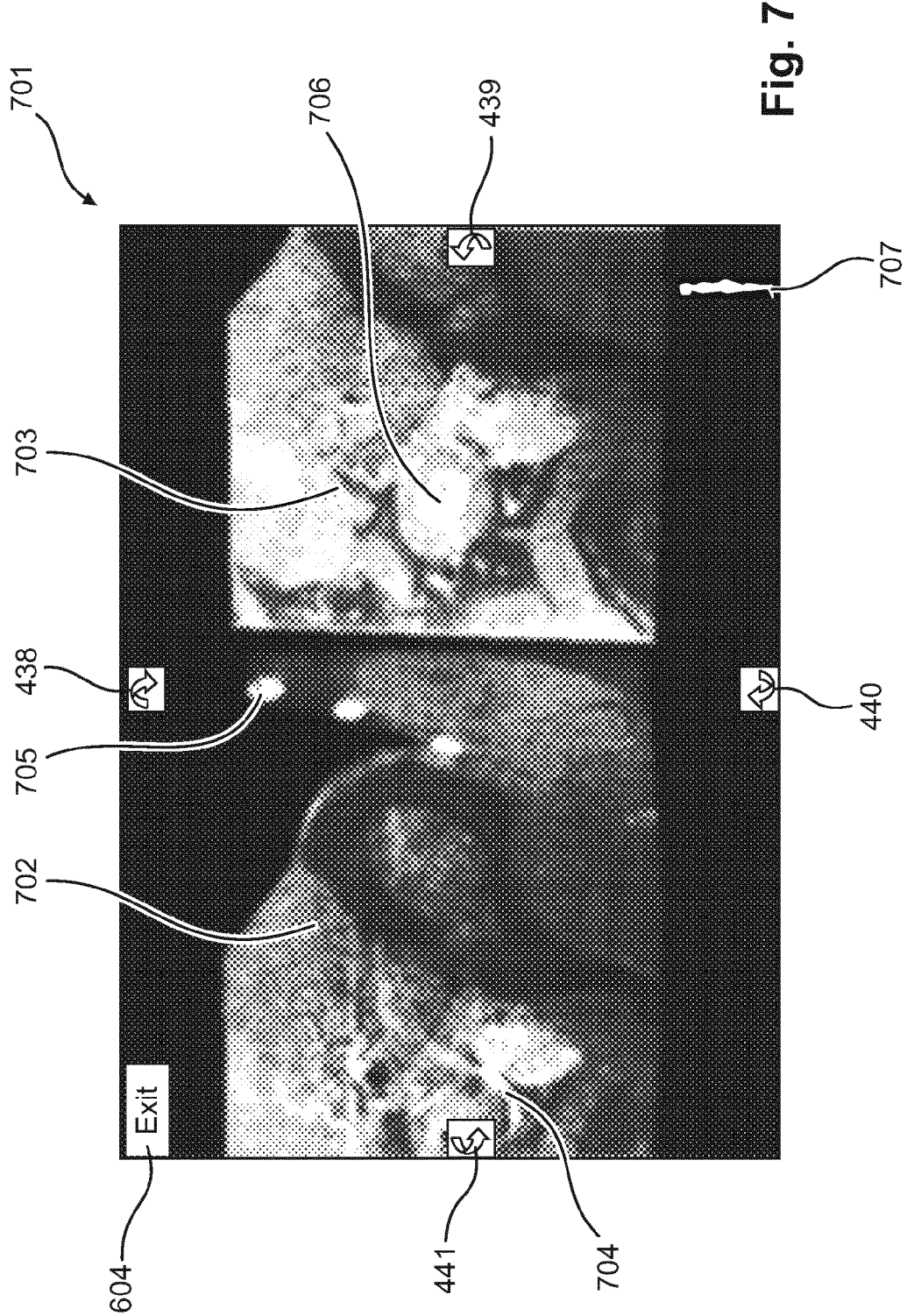
FIG. 7 shows a schematic drawing of a display view according to an exemplary embodiment of the present invention.

FIG. 7 shows a displayed image 701 of a full screen view according to an exemplary embodiment of the invention. The full screen view comprises a first image 702 with features 704 and 705. A second image 703 with a feature 706 is shown. With the button 438, 439, 440, and 441, the orientation of the first volume 103 in the object 101 can be changed. In the field 704, the orientation of the first volume 103 with respect to the object 101 is shown. With the button 604, the full screen view can be quit.

Figure 8:
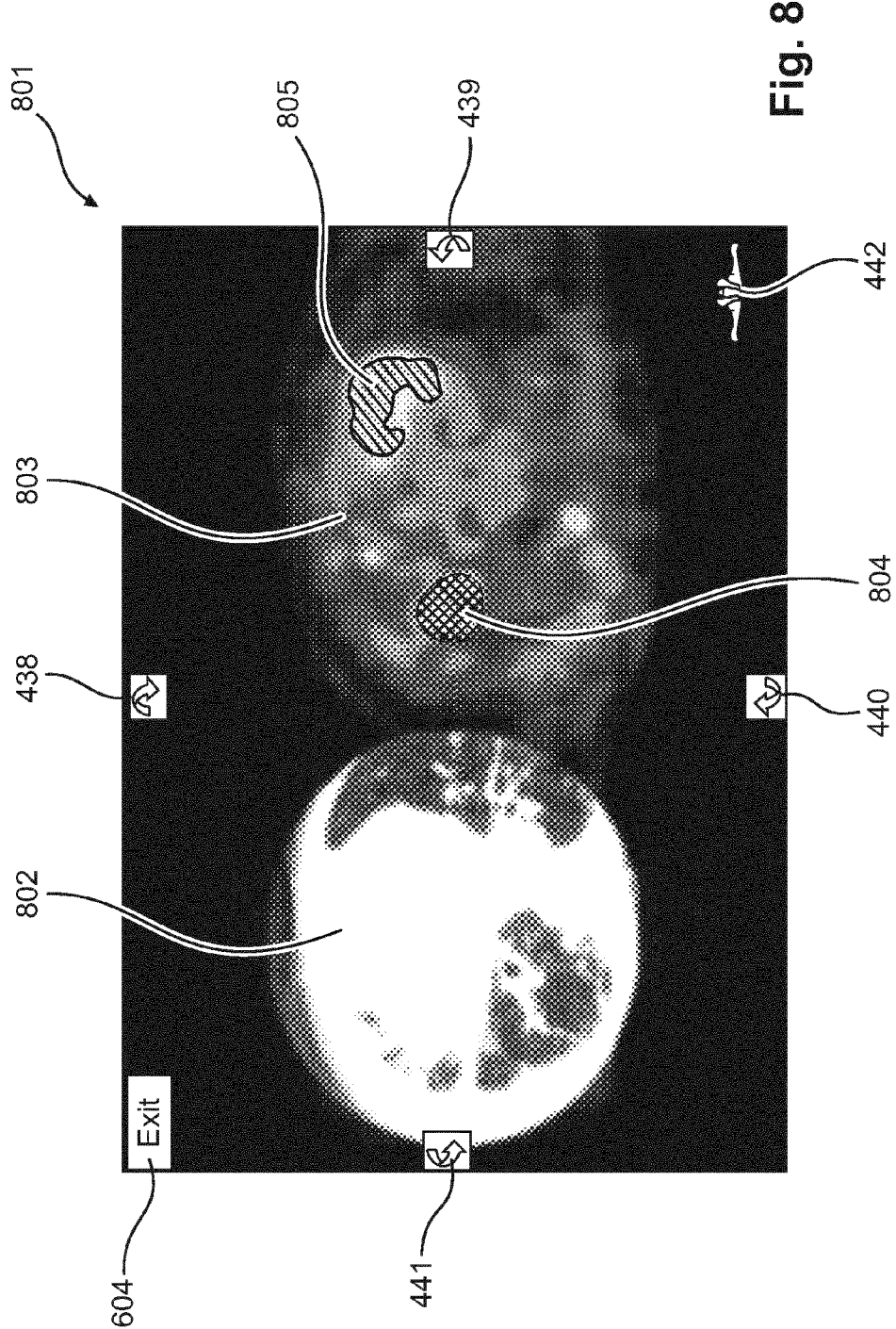
FIG. 8 shows a schematic drawing of a display view according to an exemplary embodiment of the present invention.

FIG. 8 shows a displayed image 801 of a full screen view according to an exemplary embodiment of the invention. The full screen view shows a first image 802 and a second image 803, wherein the first image 802 is recorded using a different imaging method than the second image 803. In the second image 803, further features 804 and 805 are visible.

Figure 9:
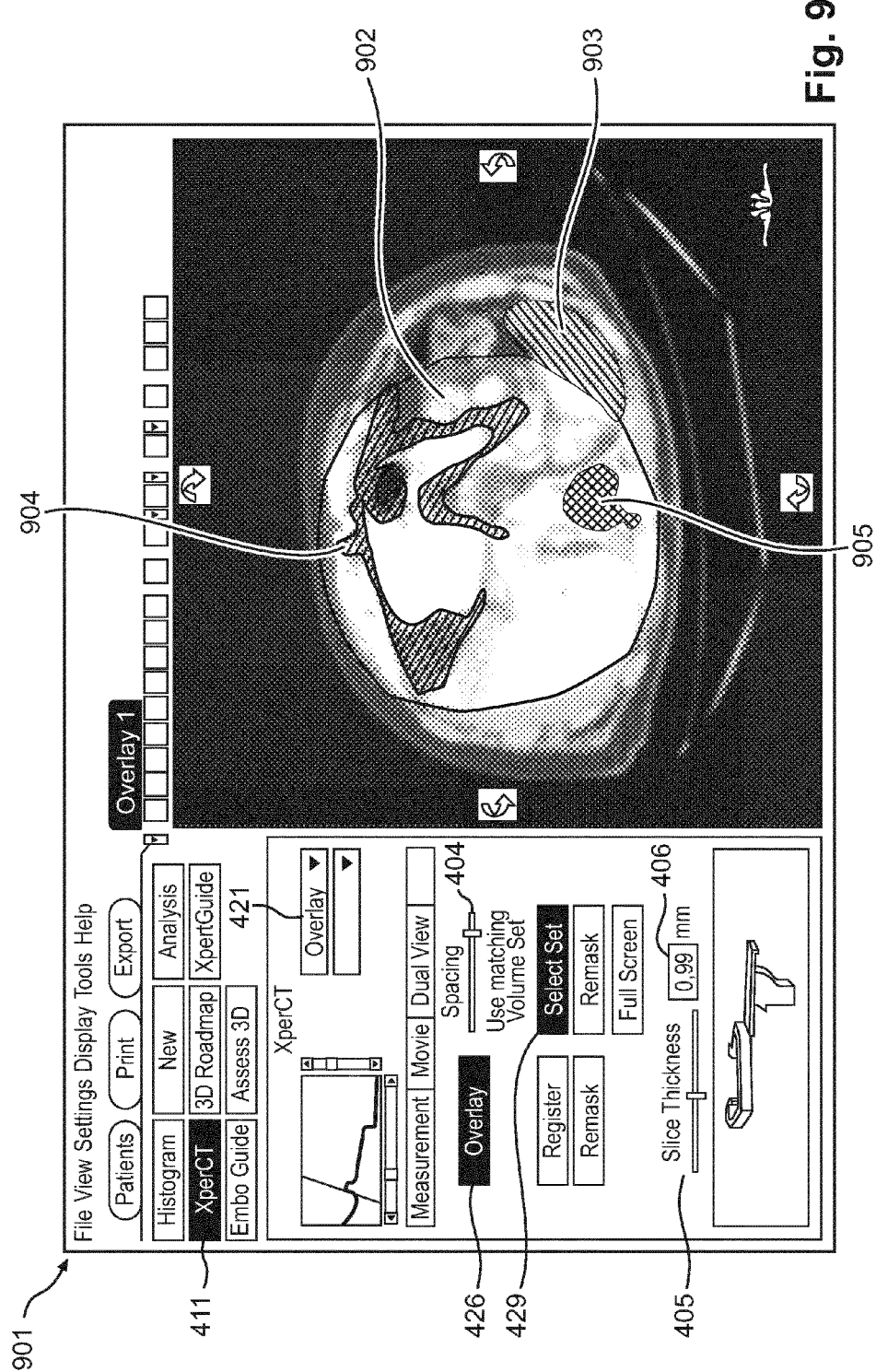
FIG. 9 shows a schematic drawing of a display view according to an exemplary embodiment of the present invention.

FIG. 9 shows a displayed image 901 according to an exemplary embodiment of the invention. The button 411 shows that the XperCT function is selected. The dropdown field 421 indicates that the overlay mode for the transfer functions is selected. Furthermore, the button 426 indicates that the Overlay function is selected and the button 429 indicates that the Select Set function is selected. With the second sliding element 405, a slab thickness of 0.98 mm is configured, which is also shown in the text field 406. With the first sliding element 404, a distance value equal to zero is selected, i.e. less or equal to the distance threshold value. Since the distance value is equal to zero and therefore less or equal to the distance threshold value, an overlay view 902 of the first image and the second image is shown. In the overlay view, features 903 belonging to the first image are shown with a first characteristic, for example, a hatching in a first direction. Features 904 belonging to the second image are shown with a second characteristic, for example, with a hatching in a second direction. Features, which are the same in the first image and the second image, are shown with both characteristics, for example, with a cross hatching. As defined above, the different hatchings may refer to different colors.

Figure 10:
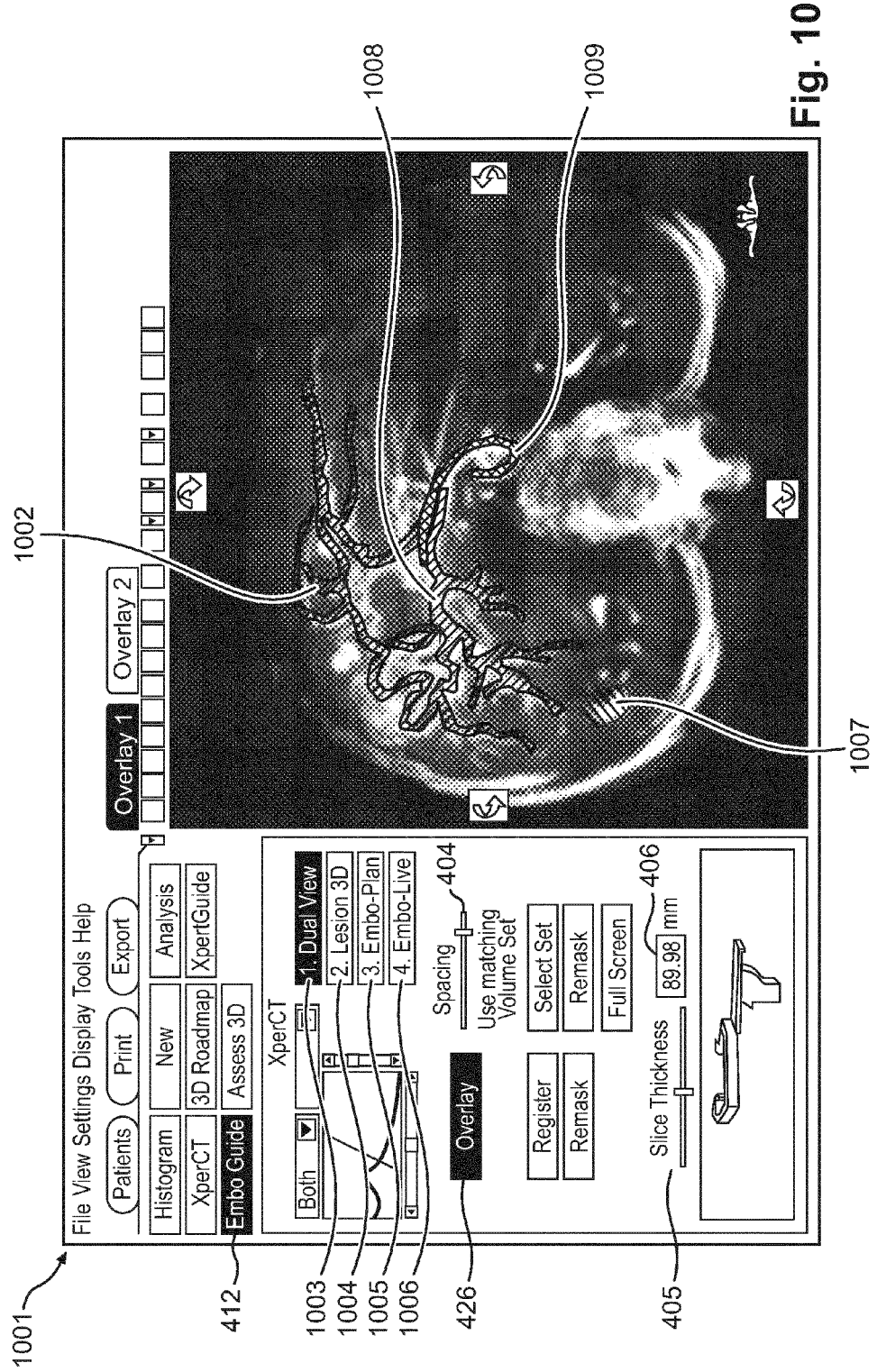
FIG. 10 shows a schematic drawing of a display view according to an exemplary embodiment of the present invention.

In FIG. 10, a displayed view 1001 according to an exemplary embodiment of the invention is shown. With the button 412, the EmboGuide function is selected. Furthermore, the controlling section comprises the button 1003 for selecting the Dual View function, button 1004 for selecting the Lesion 3D function, button 1005 for selecting the Embo Plan function, and button 1006 for selecting the Embo Live function. With button 426, the Overlay function is selected. The sliding element 405 indicates that a slab thickness of 89.98 mm is selected, which thickness is also displaced in the text field 406. With the first sliding tool 404, a distance value between an edge of the displayed first image and an edge of the displayed second image is selected, which distance value is greater than zero, i.e. greater than the distance threshold value.

The functions Dual-View, Lesion-3D, Embo-Plan and Embo-Live may provide the procedure steps that are part of the so called EmboGuide tool. The EmboGuide tool offers support for arterial embolization procedures. The dual view procedure is supporting the diagnostic step based on multi-modality information comparable to the previously described XperCT-Dual View function. The Lesion 3D function may be used to semi-automatically segment lesions in 3D. The Embo-plan function may be used for automatically feeder detection and indicates the vessel paths towards the selected lesions. The Embo-Live step may support the interventional navigation by overlaying live real-time 2D fluoro on the 3D-volume and planning information.

In the image display section, an overlay view of the first image and the second image is shown. In this exemplary embodiment, the distance threshold value is larger than zero. The provided distance value selected with the first sliding tool 404 is less or equal to the distance threshold value. Consequently, an overlay view with a superposition 1002 of the first image and the second image is shown. Features 1007 of the first image are shown with a first characteristic, for example, with a hatching in a first direction. Features 1008 belonging to the second image are shown with the second characteristic, for example, with a hatching in a second direction. Features 1009, which are the same in the first image and in the second image, are shown with the first characteristic and the second characteristic, for example, with a cross hatching.

Figure 11:
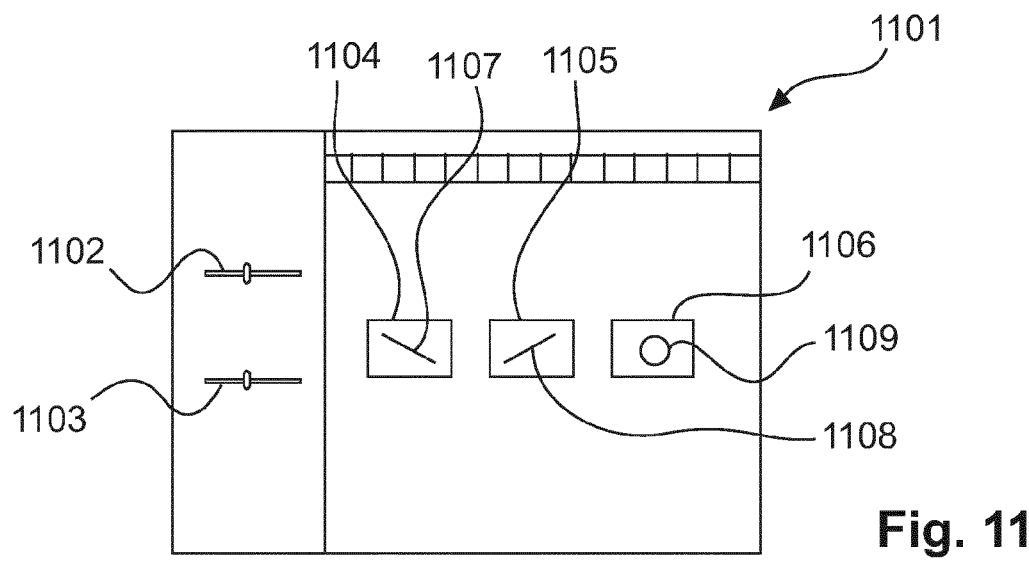
FIG. 11 shows a schematic drawing of a display view according to an exemplary embodiment of the present invention.
Figure 12:
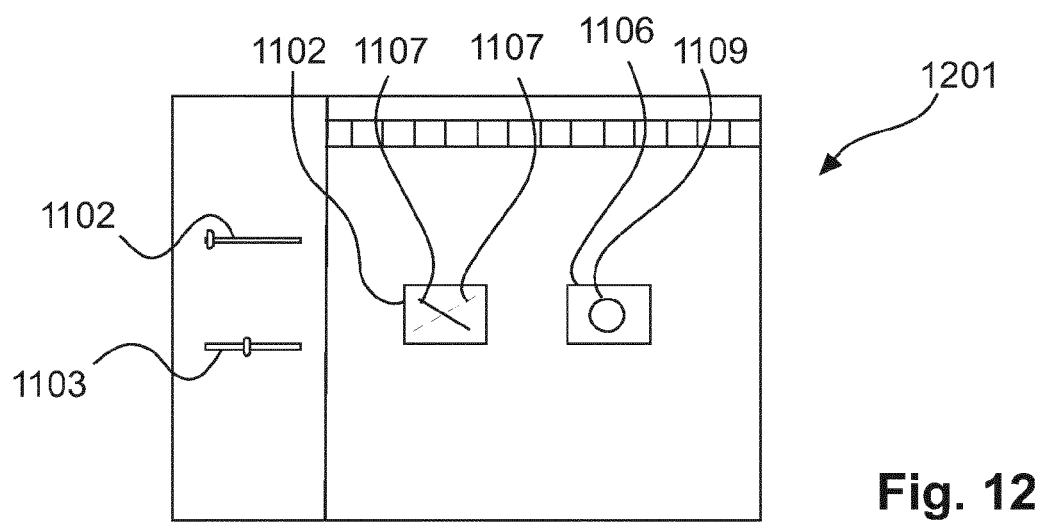
FIG. 12 shows a schematic drawing of a display view according to an exemplary embodiment of the present invention.
Figure 13:
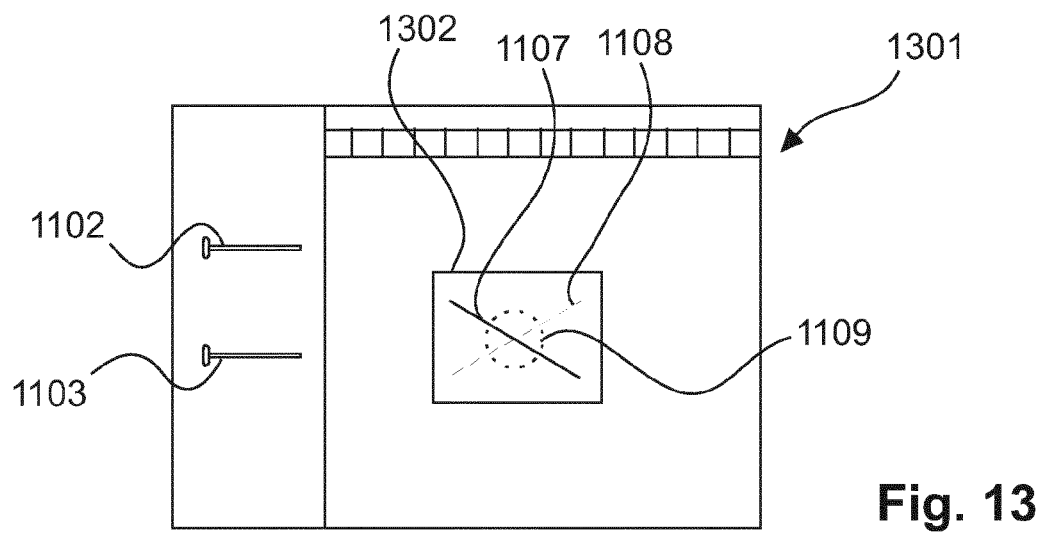
FIG. 13 shows a schematic drawing of a display view according to an exemplary embodiment of the present invention.

In FIGS. 11, 12, and 13, a displayed image for displaying three images of an object is shown. Thus, the displayed images 1101, 1201, and 1301 shown in FIGS. 11, 12, and 13 may be a result of a method for displaying at least a first image, a second image, and a third image of an object on a display, which method comprises the steps of providing a first distance value between an edge of the first image and an edge of the second image of the object, providing a second distance value between an edge of the second image and an edge of the third image of the object. Furthermore, the method comprises the steps of displaying a side by side view of the first image and the second image on the display in case the provided first distance value exceeds a first distance threshold value wherein a distance between the displayed first image and the displayed second image corresponds to the provided first distance value; displaying an overlay view of the first image and the second image in case the provided first distance value is less or equal to the first distance threshold value; displaying a side by side view of the second image and the third image on the display in case the provided second distance value exceeds a second distance threshold value, wherein a distance between the edge of the displayed second image and the edge of the displayed third image corresponds to the provided second distance value; displaying an overlay view of the second image and the third image in case the provided second distance value is less or equal to the second distance threshold value; or displaying an overlay view of the first image, the second image, and the third image in case the provided first distance value is less or equal to the first distance threshold value and the provided second distance value is less or equal to the second distance threshold value. Moreover, the method may comprise the steps of providing a first image representing a volume of the object, providing a second image representing the volume of the object, and providing a third image representing the volume of the object In the exemplary embodiments shown in FIG. 11 to FIG. 13, the distance threshold value is equal to zero. Thus, when the provided distance value is equal to zero, an overlay view of the respective images is shown and, when the provided distance value is greater than zero, a side by side view is shown. Each of the user interfaces shown in the first displayed image 1101, the second displayed image 1201, and the third displayed image 1301 comprises a sliding tool 1102 for controlling the first distance value and a sliding tool 1103 for controlling the second distance value.

In the display view 1101 shown in FIG. 11, the first sliding tool 1102 indicates that the first distance value is greater than zero and the second sliding tool 1103 indicates that the second distance value is greater than zero. Consequently, a side by side view of the first image 1104, the second image 1105, and the third image 1106 is shown, wherein a first distance between an edge of the displayed first image 1104 and an edge of the displayed second image 1105 corresponds to the first distance value, and wherein a second distance between an edge of the displayed second image 1105 and an edge of the displayed third image 1106 corresponds to the second distance value. The first image comprises a first feature 1107, the second image 1105 comprises a second feature 1108, and the third image 1106 comprises a third feature 1109.

In the display view 1201 shown in FIG. 12, the first sliding tool 1102 indicates that the first distance value is equal to zero and the second sliding tool 1103 indicates that the second distance value is greater than zero. Consequently, an overlay view 1202 of the first image and the second image is shown. The overlay view 1202 comprises the first feature 1107 of the first image with a first characteristic, for example, as a straight line and the second feature 1108 of the second image shown with a second characteristic, for example, as a dashed line. The third image 1106 is shown next to the superposition 1202 of the first image 1104 and the second image 1105, wherein a distance between the displayed superposition 1202 and the displayed third image 1106 corresponds to the second distance value.

In the displayed image 1301 shown in FIG. 13, the first sliding tool 1102 indicates that the first distance value is equal to zero and the second sliding tool 1103 indicates that the second distance value is equal to zero. Consequently, the superposition 1302 of the first image 1104, the second image 1105, and the third image 1106 is shown. The first feature 1107 belonging to the first volume 103 is shown with a first characteristic, for example, as a straight line, the second feature 1108 belonging to the second volume 104 is shown with a second characteristic, for example, as a dashed line, and the third feature 1109 belonging to the third volume is shown with a third characteristic, for example, as a dotted circle.

Other variations to the disclosed embodiments can be understood and effected by those skilled in the art in practicing the claimed invention, from a study of the drawings, from the disclosure, and from the appended claims.

In the claims, the word "comprising" does not exclude other elements or steps and the indefinite article "a" and/or "an" does not exclude a plurality.

A single processor or other unit may fulfill the functions of several item recited in the claims.

The mere fact that certain measures are recited in mutually different dependent claims does not indicate that the combination of these measures cannot be used to advantage.

The reference numerals in the claims are not intended to restrict the scope of the claims.

LIST OF REFERENCE SIGNS 101 object
102 volume of interest
103 first volume
104 second volume
106 thickness of the first volume
201 providing a distance value
202 providing a first image
203 providing a second image
204 displaying a side by side view
205 displaying an overlay view
301 assembly for calculating and displaying a display mode of at least a first volume and a second volume of an object
302 device for calculating a display mode of at least a first volume and a second volume of an object
303 processor
304 display
305 display
306 keyboard
307 mouse
308 data of a distance value
309 data of a distance threshold value
310 data of a volume of interest
311 database
312 first display signal
313 second display signal
314 toolbar
315 first sliding tool
316 second sliding tool
317 first image
318 second image
319 second feature
320 first feature
321 toolbar
322 first sliding tool
323 second sliding tool
324 superposition image
325 first feature
326 second feature
327 displayed image
328 displayed image
401 displayed image
402 toolbar
403 image displaying section
404 first sliding tool
405 second sliding tool
406 input field
407 Patients button
408 Print button
409 Export button
410 Histogram button
411 XperCT button
412 EmboGuide button
413 New button
414 3D Roadmap button
415 Assess 3D button
416 Analysis button
417 XperGuide button
418 Transfer function field
419 Transfer function graph
420 intersecting line
421 first Transfer function dropdown field
422 second Transfer function dropdown field
423 Measurement button
424 Movie button
425 Dual View button
426 Overlay button
427 Register button
428 Remask button
429 Select set button
430 Remask button
431 Full screen button
432 imaging device illustration
433 first image
434 second image
435 first tab for the first overlay
436 second tab for the second overlay
437 third tab for the third overlay
438 first rotation button
439 second rotation button
440 third rotation button
441 fourth rotation button
442 orientation graphics
501 displayed image
505 superposition image
506 feature
507 feature
508 feature
601 displayed image
602 first image
603 second image
604 exit button
605 feature
606 feature
607 feature
608 feature
609 feature
701 displayed image
702 first image
703 second image
704 feature
705 feature
706 feature
707 orientation graphics
801 displayed image
802 first image
803 second image
804 feature
805 feature
901 displayed image
902 superposition image
903 feature
904 feature
905 feature
1001 displayed image
1002 superposition image
1003 Dual View button
1004 Lesion 3D button
1005 Embo-Plan button
1006 Embo-Live button
1007 feature
1008 feature
1009 feature
1101 displayed image
1102 sliding tool
1103 sliding tool
1104 first image
1105 second image
1106 third image
1107 first feature 1108 second feature
1109 third feature
1201 displayed image
1202 superposition image
1301 displayed image
1302 superposition image

The invention claimed is:

1. A method for displaying at least a first image and a second image of an object on a display, the method comprising the steps of:
 providing a distance value between an edge of the first image and an edge of the second image of the object;
 automatically displaying a side by side view of the first image and the second image on the display in case the provided distance value exceeds a distance threshold value, wherein a distance between the edge of the displayed first image and the edge of the displayed second image corresponds to the provided distance value; or
 automatically displaying an overlay view of the first image and the second image in case the provided distance value is less than the distance threshold value.

2. The method according to claim 1, the method further comprising the steps of:
 continuously amending the distance value by means of a distance value determining device; and
 continuously adapting the displaying of the first image and the second image simultaneously to the continuous amendment based on the distance value, respectively.

3. The method according to claim 1,
 wherein in the side by side view the first image and the second image are represented in different regions of the display; and
 wherein in the overlay view the first image and the second image are combined and represented in the same region of the display.

4. The method according to claim 1, the method further comprising the step of:
 adding a first color information and/or a first intensity information of the first image to a second color information and/or a second intensity information of the second image in case the provided distance value is less than the distance threshold value.

5. The method according to claim 1, the method further comprising the steps of:
 providing a volume of interest of the object by means of volume metadata;
 selecting a first volume from the volume of interest; and
 selecting a second volume from the volume of interest.

6. The method according to claim 1,
 wherein the distance threshold value is equal to zero.

7. The method according to claim 1,
 wherein in the overlay view a superposition of the first image and the second image is displayed;
 wherein the first image is rendered with a first color and the second image is rendered with a second color; and
 wherein the first color is different to the second color.

8. The method according to claim 7,
 wherein the first color is complementary to the second color such that features that are the same in the first and second images are displayed in white in the overlay view.

9. The method according to claim 1, further comprising the steps of:
 providing a second distance value between an edge of the second image and an edge of a third image of the object;
 displaying a side by side view of the second image and the third image on the display in case the provided second distance value exceeds a second distance threshold value; wherein a distance between the edge of the displayed second image and the edge of the displayed third image corresponds to the provided second distance value;
 displaying an overlay view of the second image and the third image in case the provided second distance value is less than the second distance threshold value; or
 displaying an overlay view of the first image, the second image, and the third image in case the provided first distance value is less than the first distance threshold value and the provided second distance value is less than the second distance threshold value.

10. A non-transitory computer readable medium carrying software configured to control a computer processor to perform the method according to claim 1.

11. A device for calculating a display mode for displaying at least a first image and a second image of an object, the device comprising:
 a processor;
 wherein the device is configured to receive data of a distance value between an edge of the first image and an edge of the second image of the object;
 wherein the processor is configured to automatically generate a first display signal comprising information of a side by side view of the first image and the second image in case the distance value exceeds a distance threshold value, wherein a distance between the edge of displayed first image and the edge of the displayed second image corresponds to the provided distance value; and
 wherein the processor is configured to automatically generate a second display signal comprising information of an overlay view of the first image and the second image in case the distance value is less than the distance threshold value.

12. The device according to claim 11, the device further comprising:
 a display device configured to display a first image based on the first display signal and a second image based on the second display signal; and
 a distance value determining device configured to determine the distance value and to create corresponding data of the distance value.

13. The device according to claim 11, wherein the processor is further configured to:
 receive a volume of interest of the object by means of volume metadata;
 select a first volume from the volume of interest; and
 select a second volume from the volume of interest.

14. The device according to claim 11, wherein the processor is further configured to:
 receive a second distance value between an edge of the second image and an edge of a third image of the object;
 control a display device to display a side by side view of the second image and the third image in case the provided second distance value exceeds a second distance threshold value, wherein a distance between the edge of the displayed second image and the edge of the displayed third image corresponds to the provided second distance value;
 control the display device to display an overlay view of the second image and the third image in case the provided second distance value is less than the second distance threshold value; or control the display device to display an overlay view of the first image, the second image, and the third image in case the provided first distance value is less than the first distance threshold value and the provided second distance value is less than the second distance threshold value.

15. The device according to claim 11, wherein the overlay view is a superposition of the first image and the second image;

wherein the first image is rendered with a first color and the second image is rendered with a second color; and wherein the first color is complementary to the second color such that features that are the same in the first and second images fade toward white in the overlay view.

16. A system for displaying at least a first diagnostic image of a subject and a second diagnostic image of said subject, the system comprising:

a display device;

one or more processors configured to:

receive the first diagnostic image, the second diagnostic image and a threshold distance value;

control the display device to display the first and second diagnostic image in a side by side view; and in response to a distance between corresponding structures of the first and second diagnostic images being closer than the threshold distance, control the display device to automatically display the first and second diagnostic images in an overlay view.

17. The system according to claim 16, wherein the corresponding structures in the first and second diagnostic images include corresponding volumes of interest.

18. The system according to claim 16, wherein the one or more processors are further configured to:

receive a second threshold distance value and a third diagnostic image of said subject;

control the display device to display the second and third diagnostic images in the side by side view; and in response to a second distance between the corresponding structures of the second and third diagnostic images being less than the second threshold distance value, control the display device to automatically display the second and third diagnostic images in the overlay view, or in response to the second distance between the corresponding structures of the second and third diagnostic images being less than the second threshold distance value, and the first distance between the corresponding structures of the first and second diagnostic images being less than the first threshold value, control the display device to automatically display the first, second, and third diagnostic images in the overlay view.

19. The system according to claim 16, wherein the overlay view is a superposition of the first image and the second image;

wherein the first image is rendered with a first color and the second image is rendered with a second color; and wherein the first color is complementary to the second color.

* * * * *